(12) United States Patent
Murray et al.

(10) Patent No.: US 12,167,846 B2
(45) Date of Patent: Dec. 17, 2024

(54) MULTI-FUNCTIONAL SURGICAL INSTRUMENT

(71) Applicant: UNIVERSITY OF FLORIDA RESEARCH FOUNDATION, INCORPORATED, Gainesville, FL (US)

(72) Inventors: John D. Murray, Jacksonville, FL (US); Wendy Ashby, Jacksonville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 44 days.

(21) Appl. No.: 17/350,631

(22) Filed: Jun. 17, 2021

(65) Prior Publication Data

US 2021/0393254 A1    Dec. 23, 2021

Related U.S. Application Data

(60) Provisional application No. 63/040,098, filed on Jun. 17, 2020.

(51) Int. Cl.
*A61B 17/04* (2006.01)
*A61B 17/076* (2006.01)

(52) U.S. Cl.
CPC ........ *A61B 17/0467* (2013.01); *A61B 17/076* (2013.01)

(58) Field of Classification Search
CPC .............. A61B 17/0467; A61B 17/076; A61B 2017/00353; A61B 17/062
See application file for complete search history.

(56) References Cited

U.S. PATENT DOCUMENTS 2,315,326 A    3/1943  Gmeiner
3,254,649 A *  6/1966  Wood .................. A61B 17/076
                                          606/205
(Continued)

FOREIGN PATENT DOCUMENTS

WO    2004006780 A1    1/2004

OTHER PUBLICATIONS

Miltex #8-17T Olsen-Hegar Needle Holder with Suture Scissors, 7 1/2' (19.1), serrated jaws, 2600 teeth PSI, Carb-N-Sert, https://www.a1medicalsales.com/product/8-17TC.html, 1 page, downloaded from Internet Dec. 7, 2018.

*Primary Examiner* — Richard G Louis
*Assistant Examiner* — David P Stein
(74) *Attorney, Agent, or Firm* — Timothy H. Van Dyke; Wolter Van Dyke Davis, PLLC

(57) ABSTRACT

Disclosed is a medical instrument that includes a first elongated arm and a second elongated arm pivotally attached at a pivoting joint. The first and second elongated arms include a distal end, a proximal end, an inner surface and an outer surface. The first and second elongated arms define, along respective inner surfaces, opposing gripping portions and opposing cutting edges adjacent to the gripping portions. The first or second elongated arms also include a flange that outwardly deflects from either the first or second distal ends and the first and second elongated arms both include an outwardly deflecting flange. Embodiments enable the cutting of sutures at surgical sites possessing numerous sutures in an expedient manner without the instrument catching the sutures. The instrument also includes functionality to remove staples at a surgical site.

8 Claims, 3 Drawing Sheets

(56) References Cited

U.S. PATENT DOCUMENTS

| | | | |
|---|---|---|---|
| 3,443,313 A | 5/1969 | Profy | |
| 5,002,554 A | 3/1991 | Korber | |
| 5,439,471 A | 8/1995 | Kerr | |
| 6,051,004 A | 4/2000 | Gill | |
| 6,976,992 B2 | 12/2005 | Sachatello et al. | |
| 2003/0171747 A1* | 9/2003 | Kanehira | A61B 18/085 606/45 |
| 2014/0012314 A1* | 1/2014 | Dai | A61B 17/2804 606/207 |
| 2014/0277516 A1* | 9/2014 | Miller | A61B 17/0642 623/18.11 |
| 2017/0049466 A1* | 2/2017 | Schmid | A61B 17/062 |
| 2018/0168568 A1* | 6/2018 | Ali | A61B 17/0467 |
| 2020/0038162 A1* | 2/2020 | Anderson | A61B 17/3201 |

\* cited by examiner

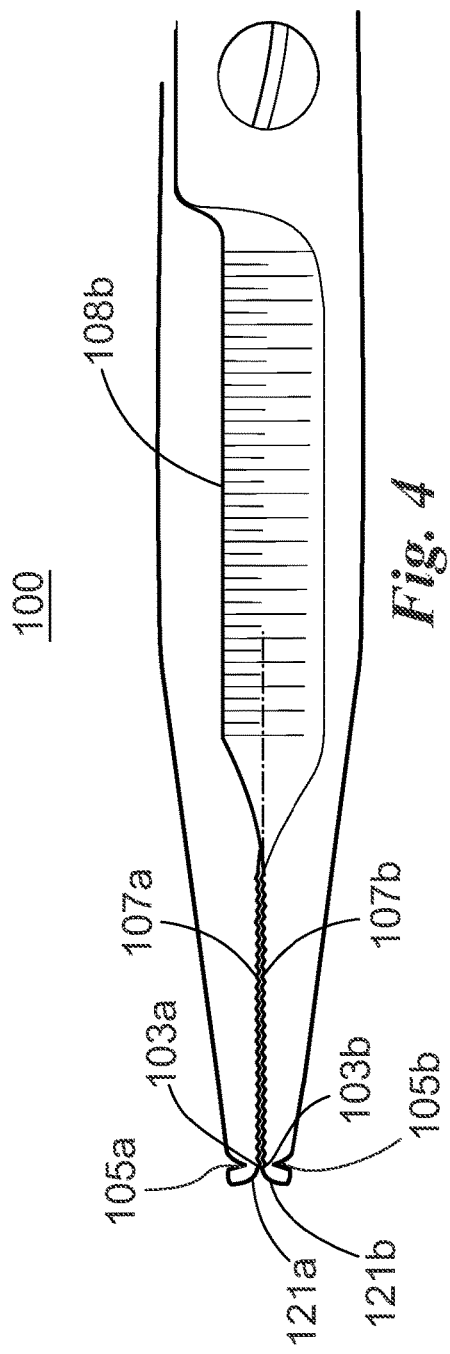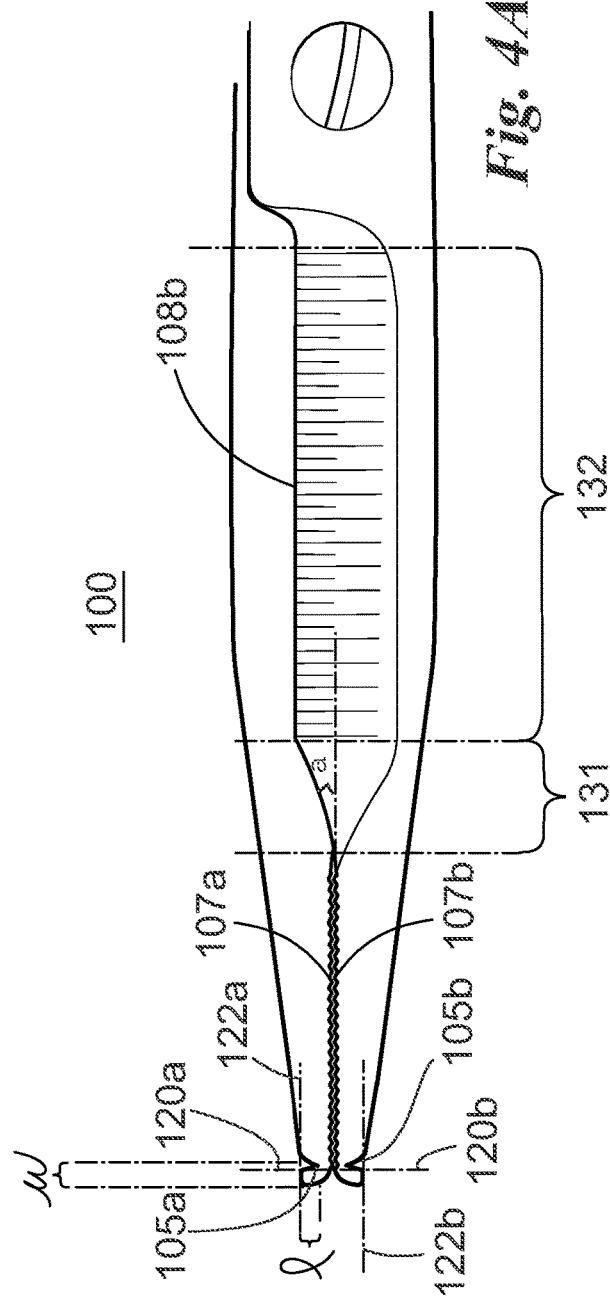

MULTI-FUNCTIONAL SURGICAL INSTRUMENT

BACKGROUND

Many different surgical devices exist that have one or more features to assist with suturing. One long-established suturing device is the Olsen-Hager device that includes a needle driver feature and a suture cutting feature. An early version of the Olsen-Hager combination needle/driver and suture cutting device is disclosed in U.S. Pat. No. 2,315,326 and has been in use as early as the 1940s. The Olsen-Hager type device is viewed as an industry standard and few efforts have been made to improve upon its functionality.

BRIEF DESCRIPTION OF THE DRAWINGS

FIG. 4 shows a side view of a section of the embodiment shown in FIG. 1.

FIG. 4A shows a side view designating length, width and degrees of certain portions of the device.

DETAILED DESCRIPTION

Figure 1:
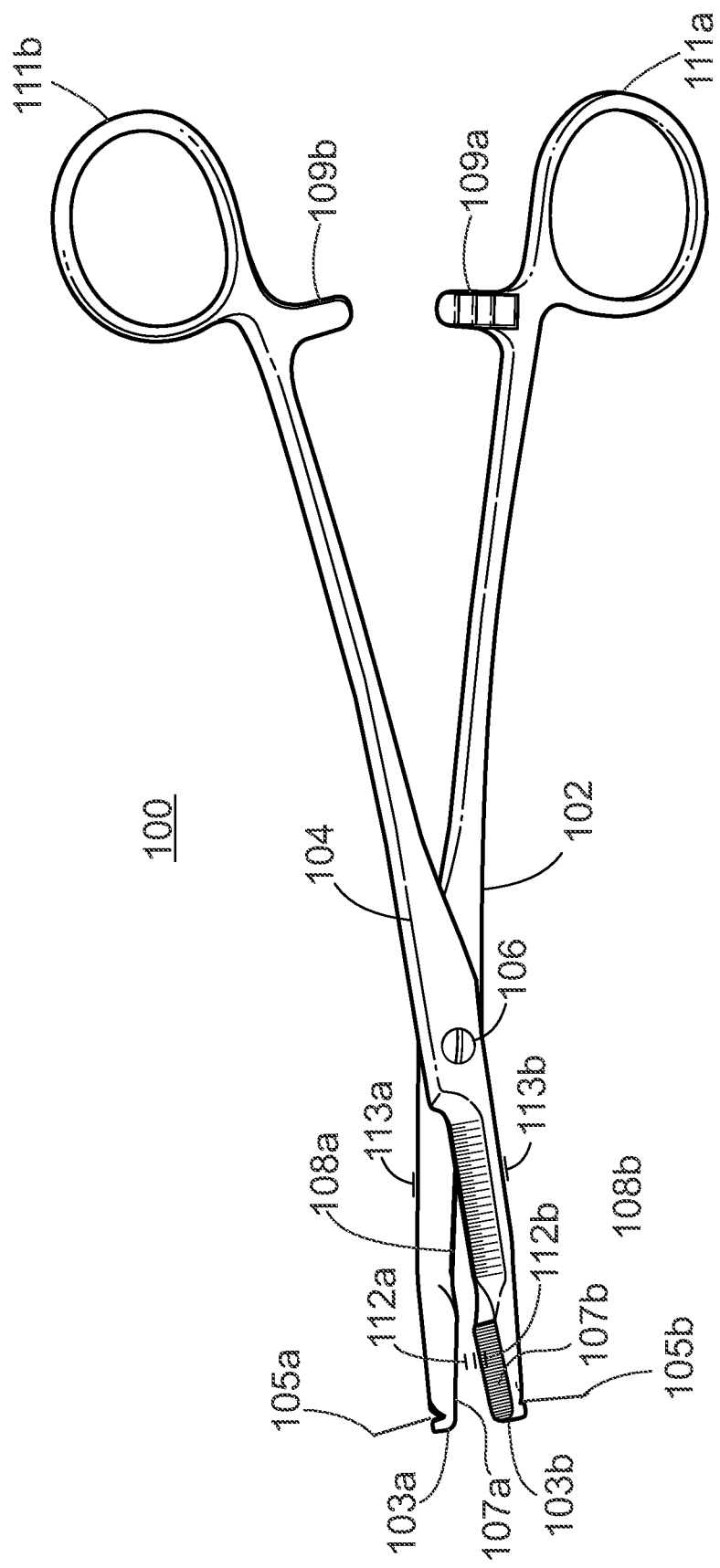
FIG. 1 shows side perspective view of an embodiment of a multi-functional surgical device.

For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated container and method, and such further applications of the principles of the invention as illustrated therein being contemplated as would normally occur to those skilled in the art to which the invention pertains.

It is to be noted that the terms "first," "second," and the like as used herein do not denote any order, quantity, or importance, but rather are used to distinguish one element from another, unless otherwise specifically stated herein. The terms "a" and "an" do not denote a limitation of quantity, but rather denote the presence of at least one of the referenced item. The modifier "about" used in connection with a quantity is inclusive of the stated value and has the meaning dictated by the context. Furthermore, to the extent that the terms "including," "includes," "having," "has," "with," or variants thereof are used in either the detailed description and/or the claims, such terms are intended to be inclusive in a manner similar to the term "comprising."

It is to be noted that all ranges disclosed within this specification are inclusive and are independently combinable. Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. As a non-limiting example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 7.

As used herein, the terms "subject", "user" and "patient" are used interchangeably. As used herein, the term "subject" refers to an animal, preferably a mammal such as a non-primate (e.g., cows, pigs, horses, cats, dogs, rats etc.) and a primate (e.g., monkey and human), and most preferably a human.

It has been realized that conventional needle driver/suture cutting devices have certain drawbacks. For example, the conventional Olsen-Hager device includes an abrupt and steep transition from the needle driver portion to the cutting edge portion. The inventor has discovered that this steep face of the transition tends to catch sutures as the surgeon attempts to position a suture at the cutting edges. This catching of sutures unnecessarily delays suturing procedures, especially when there is a high number of sutures to tie at a surgical site, or worse pulls the suture which can damage the tissue.

Also, conventional needle/driver/suturing devices lack any ability to assist in removing staples at a surgical site. Many new surgical techniques require a pre-stapling step prior to suturing. To remove a staple at a point in the surgical site and then suture that point requires a number of steps and shuffling of instruments by the surgeon.

According to one embodiment, provided is a medical instrument that includes a first elongated arm and a second elongated arm pivotally attached at a pivoting joint. The first and second elongated arms include a distal end, a proximal end, an inner surface and an outer surface. The first and second elongated arms define, along respective inner surfaces, opposing gripping portions and opposing cutting edges adjacent to the gripping portions. The first or second elongated arms also include a flange that outwardly deflects from either the first or second distal ends. In a specific embodiment, the first and second elongated arms both include an outwardly deflecting flange.

The cutting edge portions of the first and second elongated arms have a distal section and a proximal section. The distal section is configured to slope up to the proximal section to provide a smooth transition to the cutting edges. This slope avoids the aforementioned catching of the sutures as the device is moved to align a suture with the cutting edges. In a specific example, the slope is about 60 degrees or less. In a more specific embodiment, the slope is 45 degrees, 40 degrees, 30 degrees, 25 degrees, or less.

The flange includes an inner end associated with the respective first or second distal end and an outer end. The flange includes a length of about 0.5 to about 30 mm between the inner and outer ends. In a more specific embodiment, the flange has a length of about 1 to about 10 mm. In an even more specific embodiment, the flange has a length of 1-2 mm. In an alternative embodiment, the flange tapers from the inner end to the outer end. The flange also has a width spanning from the distal surface to the proximal surface, where at least a portion of the width is about 0.1 to about 3 mm. In a specific embodiment, the width of the portion is about 0.5 to about 1.0 mm.

The proximal ends of the first and second elongated arms also include a handle. In one embodiment, the handle is a ring for placement of the surgeon's finger(s). In addition, the first elongated arm further includes a first interlocking member and the second elongated arm further includes a second interlocking member, wherein the first and second interlocking members are situated proximal to the pivoting joint and releasably engage together to secure the instrument in a closed position.

According to another embodiment, disclosed is a method of conducting a surgical procedure on a surgical site of a subject, the surgical site involving open tissue that needs closure. The method includes obtaining a medical instrument embodiment described herein; applying a surgical staple to tissue at the surgical site; removing the surgical staple by wedging the first and/or second flange between the staple and the tissue; holding a needle attached to a suture using the gripping portions of the medical instrument; directing the needle into tissue at the surgical site; and cutting the suture from the needle.

DESCRIPTION OF ILLUSTRATED EMBODIMENTS

Figure 2:
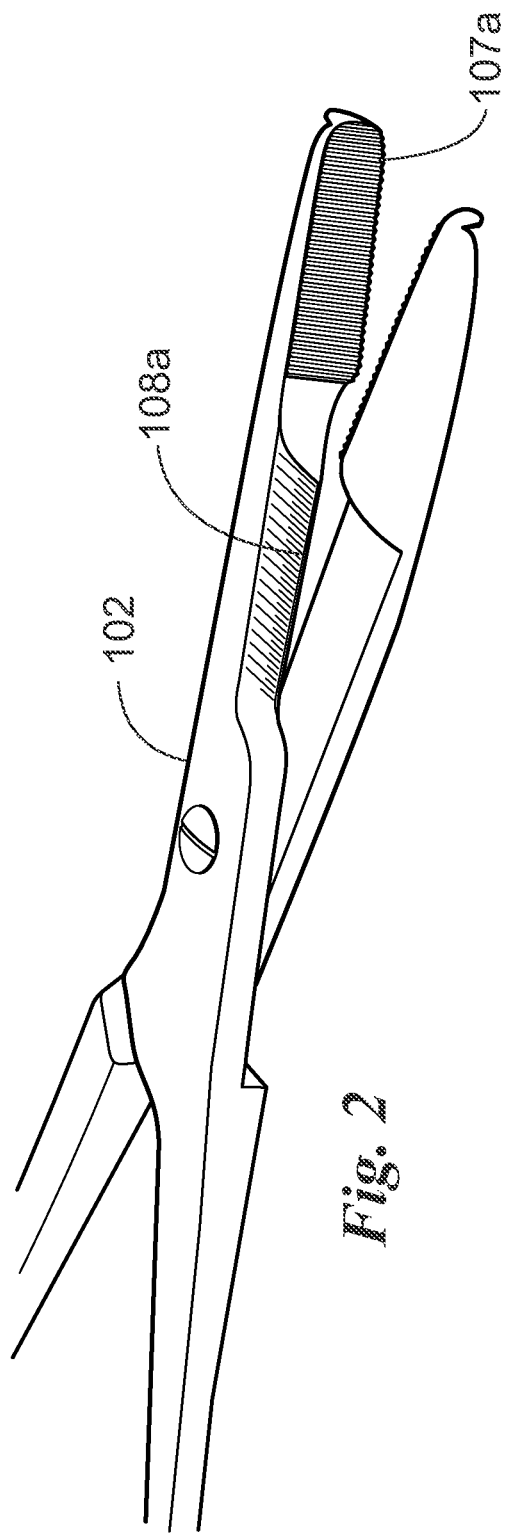
FIG. 2 shows a perspective end view of the embodiment shown in FIG. 1.

Turning to the drawings, FIG. 1 shows a side perspective view of a medical instrument embodiment 100. The medical instrument 100 includes a first elongated arm 102 and a second elongated arm 104. The first and second elongated arms each comprise a distal end 103a, 103b, a proximal end 105a, 105b, an inner surface 112a, 112b, and outer surface 113a, 113b. The first and second elongated arms 102, 104 pivot about a pivoting joint 106. One example of a pivoting joint is a mortise and tenon arrangement, where one of the elongated arms has a hole and the other has a peg that fits in the hole. Associated with the distal ends 105a,b are ring handles 111a, 111b. Also associated with the distal ends 105a,b, are first and second locking members 109a and 109b, respectively. The locking members 109a,b releasably lock together which locks the instrument 100 in a closed position, where the distal ends 103a,b are urged together. FIG. 2 shows the reverse side of a section of the instrument 100.

Figure 3:
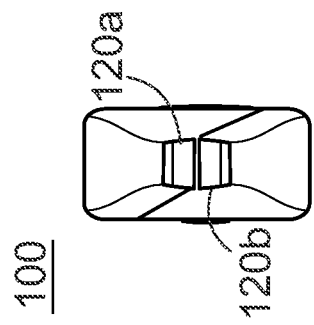
FIG. 3 shows a plan view of a distal end of the embodiment shown in FIG. 1.

FIGS. 3, 4 and 4A show an end planar view (FIG. 3) and a side view (FIGS. 4 and 4A, of the instrument 100. As shown, each of the distal ends 103a, 103b show a flange 120a, 120b, respectively, that extends outwardly from the distal ends 103, 103b, respectively. The flanges 120a, 120b each comprise an inner end 121a, 121b, respectively, and an outer end 122a, 122b, respectively. From the inner end 121a to the outer end 122b, the flange has a length l portion. The l portion may be from about 0.5-30 mm. The flanges also include portion having a width w from a distal surface to a proximal surface. The width w may be from about 0.1 to about 3 mm.

Also shown in FIG. 4A is the cutting edge 108b that has a distal portion 131 that slopes up to proximal portion 132. The angle a of the slope may be 50 degrees or less, 40 degrees or less, 30 degrees or less, or 20 degrees. It is noted that the slope does not need to be a precise straight edge but may be somewhat curved. In the case of being curved, the slope represents the average slope obtained from multiple points along the distal portion. Also, shown in FIGS. 4 and 4A are notches 105a, 105b that allow for resting of the staple when the flanges separate.

While one or more embodiments of the present invention have been shown and described herein, such embodiments are provided by way of example only. Variations, changes and substitutions may be made without departing from the invention herein. Accordingly, it is intended that the invention be limited only by the spirit and scope of the appended claims. The teachings of all references cited herein are incorporated in their entirety to the extent not inconsistent with the teachings herein.

What is claimed is:

1. A medical instrument comprising: a first elongated arm and a second elongated arm pivotally attached at a pivoting joint, the first and second elongated arms comprising a distal end, a proximal end, an inner surface and an outer surface, wherein the first and second elongated arms define, along respective inner surfaces, opposing gripping portions and opposing cutting edges proximal to the gripping portions, and wherein the first and second elongated arms comprise a flange, each flange comprising an inner end and an outer end such that the outer end outwardly deflects from the distal end of the first and second elongated arms, wherein the instrument has a longitudinal axis;

wherein the cutting edge of the first elongated arm and the cutting edge of the second elongated arm each comprise a proximal portion and a distal portion wherein the distal portion is sloped at a slope angle of 50 degrees or less relative to the longitudinal axis and the proximal portion is straight relative to the longitudinal axis;

wherein the flange comprises a length of about 0.5 to about 30 mm between the inner and outer ends; and wherein the instrument comprises a first and second notch adjacent to the flange of the first and second elongated arms, respectively, such that a staple can rest while being removed.

2. The medical instrument of claim 1, wherein the length comprises about 1 to about 2 mm.

3. The medical instrument of claim 1, wherein the first and second flanges are tapered from the respective inner ends to the outer ends.

4. The medical instrument of claim 1, wherein the flange comprises a portion comprising a width of about 0.1 to about 2 mm.

5. The medical instrument of claim 4, wherein the width comprises about 0.5 to about 1.0 mm.

6. The medical instrument of claim 1, wherein the proximal end of the first and second arms each comprise a handle.

7. The medical instrument of claim 1, wherein the first elongated arm further comprises a first interlocking member and the second elongated arm further comprises a second interlocking member, wherein said first and second interlocking members are situated proximal to the pivoting joint and releasably engage together to secure the instrument in a closed position.

8. A method of conducting a surgical procedure on a surgical site of a subject, the method comprising obtaining a medical instrument comprising: a first elongated arm and a second elongated arm pivotally attached at a pivoting joint, the first and second elongated arms comprising a distal end, a proximal end, an inner surface and an outer surface, wherein the first and second elongated arms define, along respective inner surfaces, opposing gripping portions and opposing cutting edges proximal to the gripping portions, and wherein the first and second elongated arms comprise a flange, each flange comprising an inner end and an outer end such that the outer end outwardly deflects from the distal end of the first and second elongated arms, wherein the flange comprises a length of about 0.5 to about 30 mm between the inner and outer ends; and wherein the instrument comprises a first and second notch adjacent to the flange of the first and second elongated arms, respectively, such that a staple can rest while being removed;

wherein the instrument has a longitudinal axis;

wherein the cutting edge of the first elongated arm and the cutting edge of the second elongated arm each comprise a proximal portion and a distal portion wherein the distal portion is sloped at a slope angle of 50 degrees or less relative to the longitudinal axis and the proximal portion is straight relative to the longitudinal axis;

applying a surgical staple to tissue at the surgical site;

removing the surgical staple by wedging the flange between the staple and the tissue;

holding a needle attached to a suture using the gripping portions of the medical instrument;

directing the needle into tissue at the surgical site; and cutting the suture from the needle.

* * * * *